US00PP08588P

United States Patent [19]

Stravers

[11] Patent Number: Plant 8,588

[45] Date of Patent: Feb. 8, 1994

[54] GERBERA PLANT "TERFARO"

[75] Inventor: Lambertus J. M. Stravers, Kudelstaart, Netherlands

[73] Assignee: Terra Nigra B.V., De Kwakel, Netherlands

[21] Appl. No.: 942,279

[22] Filed: Sep. 9, 1992

[30] Foreign Application Priority Data

Dec. 18, 1990 [NL] Netherlands ..... GRB 1188

[51] Int. Cl.[5] ..... A01H 5/00

[52] U.S. Cl. ..... Plt./68.1

[58] Field of Search ..... Plt. 68.1

*Primary Examiner*—James R. Feyrer
*Assistant Examiner*—Elizabeth C. Kemmerer

[57] ABSTRACT

A new and distinct cultivar of Gerbera plant names 'Terfaro', characterized by its single type, a red ray floret which is a solid red color throughout, a green disc floret the outermost petaloids of which are red and display yellow stigmas and anthers, red perianth lobe color and 110 mm overall flower diameter is disclosed.

1 Drawing Sheet

BACKGROUND OF THE INVENTION

The present invention comprises a new and distinct cultivar of *Gerbera jamesonni*, referred to by the cultivar name 'Terfaro', 'Terfaro' was originated from a hybridisation program in De Kwakel, The Netherlands in 1989. The female parent was 'Terfacci' -87.354- (registration number 10786; Mar. 4, 1991), U.S. Plant Pat. No. 7,848. The male parent was 'Terdelfino' -82.250- (registration number 10016; Feb. 20, 1990) and was available to others outside the company. Female parent 'Terfacci' distinguishes from 'Terfaro' by its higher production, smaller flower-diameter, stronger stems and a soft color pink. The male parent 'Terdelfino' is a semi-double type and has a darker red color. The new cultivar was selected by me from the progeny of the stated parentage on or about November 1989. The first asexual reproduction of 'Terfaro' was accomplished when vegetative cuttings were taken on April 1990 in De Kwakel. The new cultivar is presently being propagated by cuttings and tissue culture. Horticultural examination of selected units initiated November 1990 has demonstrated that the combination of characteristics as herein disclosed for 'Terfaro' are firmly fixed and are retained through successive generations of asexual reproduction. The following observations, measurements and comparisons describe plants grown in De Kwakel, The Netherlands, under greenhouse conditions which closely approximate those generally used in commercial practice. The following traits have been repeatedly observed and are determined to be basic characteristics of 'Terfaro', which in combination distinguish this Gerbera from its parents and all other varieties of which I am aware:

1. Type Single.
2. Color of ray floret: Very distinctive red.
3. Color of disc floret: Green.
4. Color of perianthy lobe: Red.
5. Diameter of flower head: Medium 110 mm.

Of the many commercial cultivars known to me, there is no cultivar similar in comparison to 'Terfaro'.

BRIEF DESCRIPTION OF THE FIGURE OF THE DRAWING

The accompanying photographic drawing shows typical inflorescence and foliage characteristics nearly true as possible. In the following description, color references are made to The Royal Horticultural Society Color Chart (RHS). The color values were determined at 10.30 a.m. on Nov. 12, 1990 under natural light at De Kwakel.

BOTANICAL DESCRIPTION OF THE PLANT

Botanical: *Gerbera jamessonii* cv Terafaro.

1. INFLORESCENCE

A. Capitulum:
- *Form.*—Cup shaped.
- *Type.*—Single.
- *Diameter across face.*—100 mm.

B. Corolla of ray florets:
- *Color (general tonality from a distance of 3 meters-).*—Red.
- *Color (topside).*—RHS 44A.
- *Color (bottom).*—RHS 33A-32C.

C. Corolla of disc florets:
- *Color (mature).*—Green RHS 150C.
- *Color (immature).*—Green RHS 150C.

D. Reproductive organs:
- *Stigma.*—Yellow RHS 13B.
- *Anthers.*—Light yellow RHS 14A.
- *Pappus.*—Yellow RHS 12D.

2. PLANT

A. General appearance:
- *Height.*—40–45 cm.

B. Foliage:
- *Color (abaxial).*—RHS 147A.
- *Color (adaxial).*—RHS 147B.
- *Shape.*—The angle of apex: weakly obtuse. The shape of apex: rounded. The margin of lobes: crenate.

C. Disease resistance: No special disease resistance.

3. OTHER CHARACTERISTICS

The following traits have been repeatedly observed and are determined to be basic characteristics of 'Terfaro', which in combination distinguish this Gerbera as a new and distinct cultivar.

Leaf blade:

*Length.*—Medium (55 cm).

*Width.*—Medium (15 cm).

*Thickness.*—Medium.

*Blistering.*—Medium.

*Pubescence.*—On upper side (midrib excluded) of the leaf blade is absent.

*Depth of cuts or incisions in leaf.*—Basal part: Deep. Central part: Medium. Distal part: Shallow.

*Color.*—Upperside of the leaf blade is dark green (RHS 147A).

*Glossiness on upper side.*—Medium.

*Angle of apex.*—Weakly obtuse.

*Shape of apex.*—Rounded.

*Margin of lobes.*—Crenate.

*Extensions of margin.*—Small.

*Petiole length.*—Medium.

*Petiole anthocyanin coloration.*—Medium.

*Petiole anthocyanin coloration.*—Present.

Peduncle:

*Length.*—Medium (70 cm).

*Cross section.*—Round.

*Tendency to fasciation.*—Absent.

*Thickness.*—Medium.

*Strength.*—Medium.

*Pubescence.*—Medium.

*Color.*—Medium green.

*Anthocyanin coloration.*—*At base: Very strong. At top: Absent.*

*Involucral bracts.*—Absent.

Flower head:

*Type.*—Single.

*Diameter.*—Medium (approx. 110 mm).

*Involucre.*—Height: Medium (16 mm). Diameter: Medium. Number of bracts: Medium (56). Longitudinal axis of bracts of iner rows: Straight. Anthocyanin: Absent. Pubescence: Medium.

*Ray florets.*—Number: Large (80). Shape: Elliptic. Longitudinal axis outer row: Reflexing. Longitudinal axis inner row: Straight.

*Outer ray florets.*—Cross section: Flat. Length: Medium (55 mm). Width: Medium. Longitudinal folding: Medium. Angle of apex: Right. Shape of apex: Rounded. Incisions of apex: present. Number: Two. Depth: Shallow. Length of free petals: Short. Color distribution on inner side: Uniform. Edge of different color: Absent. Striation: Absent. Claw spot: Absent.

Disc florets:

*Diameter.*—Medium.

*Main color perianth lobes.*—Red for both female and male flowers (RHS 44A). The disc florets are green in the center and red near the perimeter of the disc floret. The florets near the perimeter of the disc floret display yellow stigmas and anthers.

Reproductive parts:

*Stigma.*—Main color yellow (RHS 13B).

*Anthers.*—Main color light yellow (RHS 14A). Color of top relative to other parts is identical. Longitudinal striping: Absent.

*Pappus.*—Main color yellow (RHS 12D). Color of top relative to other parts is lighter. Orientation: Level of top relative to closed disc florets is the same.

*Fertility.*—Fertility is very good with good seed setting.

I claim:

1. A new and distinct cultivar of Gerbera plant named 'Terfaro', as illustrated and described, characterized by its single type, a red ray floret which is a solid red color throughout, a green disc floret the outermost petaloids of which are red and display yellow stigmas and anthers, red perianth lobe color and 110 mm overall flower diameter.

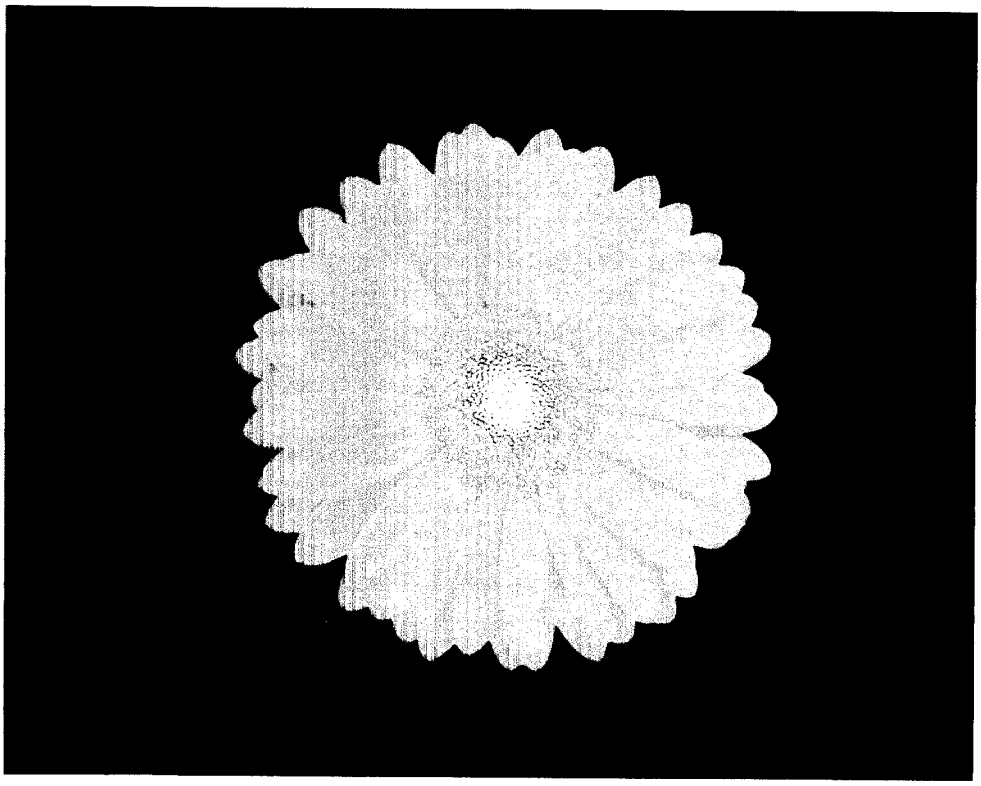

* * * * *